United States Patent [19]

Rosenbush

[11] Patent Number: 5,486,659
[45] Date of Patent: Jan. 23, 1996

[54] STETHOSCOPE PROTECTION DEVICE AND METHOD FOR USING SAME

[76] Inventor: Stuart W. Rosenbush, 6643 N. Le Mai Ave., Lincolnwood, Ill. 60646-3101

[21] Appl. No.: 207,833

[22] Filed: Mar. 8, 1994

[51] Int. Cl.⁶ .................................... A61B 7/02
[52] U.S. Cl. .......................... 181/131; 181/137
[58] Field of Search ................. 181/131, 137; 128/715, 773, 798, 639; 381/67

[56] References Cited

U.S. PATENT DOCUMENTS 4,871,046  10/1989  Turner ...................................... 181/131
5,172,683  12/1992  West ...................................... 181/131 X Primary Examiner—Khanh Dang

[57] ABSTRACT

Stethoscope-protecting bags for protecting a stethoscope from contamination during a stethoscopic examination are provided.

9 Claims, 4 Drawing Sheets

5,486,659

STETHOSCOPE PROTECTION DEVICE AND METHOD FOR USING SAME

FIELD OF THE INVENTION

The present invention relates generally to the use of stethoscopes and more particularly to novel disposable bags for protecting a stethoscope from being soiled, especially by microorganisms, as a result of a routine stethoscopic examination.

BACKGROUND OF THE INVENTION

Today, patients who require hospitalization for medical or surgical treatment generally are seriously ill. Such patients may undergo surgical procedures or may have open wounds which can be the source of disease transmission due to blood exposure and drainage of various bodily fluids.

Despite the significant advances in medical technology, stethoscopes remain an invaluable tool for taking care of patients. Medical care providers, such as doctors and nurses, routinely employ stethoscopes to examine the chests, abdomens, and other areas of patients. These areas may be secreting body fluids contaminated with infectious agents, including viruses such as human immunodeficiency virus (HIV), thereby resulting in contamination of the stethoscope head. Inadvertently exposing a person having an open cut or wound to a stethoscope harboring infectious agents poses a potentially serious risk of disease.

Today physicians and nurses usually use their own stethoscopes without specific preventive measures. For example, it is common, after examining a patient, to merely wipe the stethoscope off with a paper towel and/or alcohol.

Alternatively, disposable stethoscopes are available, especially in intensive care units or wards where AIDS patients are located. These disposable stethoscopes are relatively inexpensive, but of poor quality. They may be adequate for hearing certain obvious abnormalities, but less obvious findings are usually not possible to evaluate and subtle findings almost certainly go undetected.

Also, the choice of a stethoscope is a personal decision which is based on testing and evaluation of various available models. Some models of stethoscopes may fit the ears of one individual better than other models, and some allow detection of subtle findings that may not be heard with others. The high quality stethoscopes are of course expensive, and to make a disposable stethoscope which provides excellent sound quality is not practical.

At the present time there exists essentially two alternatives: A medical worker may use a disposable, inexpensive but often inadequate and ill-fitting stethoscope, or use a high quality instrument which, even with normal precautions, can remain unintentionally contaminated. It would be very desirable to combine the advantages of high quality stethoscopes with those of disposable stethoscopes, such that high quality stethoscopes may be used with greatly reduced risk for disease transmission.

SUMMARY OF THE INVENTION

The present invention, in one of its embodiments, entails an examination kit comprising a conventional stethoscope (having a head portion for transducing sound waves which travel through a pair of tubes terminating in earpieces); and a stethoscope protecting bag which is adapted to receive at least the head portion of the stethoscope.

In another of its aspects the present invention entails a stethoscope bag adapted to receive at least the head portion of a stethoscope, which bag is provided with perforations along at least a portion of its lateral edges to allow separation of the front and rear panels of the bag. Separation of the panels facilitates removal of the bag from the stethoscope after use.

The present invention further entails a stethoscope protecting bag having interior dimensions which are decreased or stepped-down in the region of the closed end of the bag so that the inner walls of the bag elastically deform to positively engage the head of a stethoscope. When the stethoscope head is inserted into the bag and urged slightly past the point where the bag fits snugly on the head of the stethoscope, the bag is maintained in place by the slight elastic deformation. This allows the bag to be conveniently maintained on the stethoscope during use.

In another embodiment, the present invention entails a stethoscope protecting bag having a first length with interior dimensions suitable for receiving the stethoscope head, an area of reduced interior dimensions which, when elastically deformed, allows the stethoscope head to pass, and a second length of bag having with interior dimensions suitable for receiving the stethoscope head (i.e., relatively enlarged with respect to the area of reduced interior dimensions). The first and second portions of the stethoscope protecting bag are separated by the area of reduced interior dimensions. In this embodiment of the present invention, the head of the stethoscope is urged past the area of reduced interior dimensions, by elastic deformation thereof, and retained within the second portion (proximal to the closed end) of the bag.

DETAILED DESCRIPTION OF THE INVENTION

Figure 1:
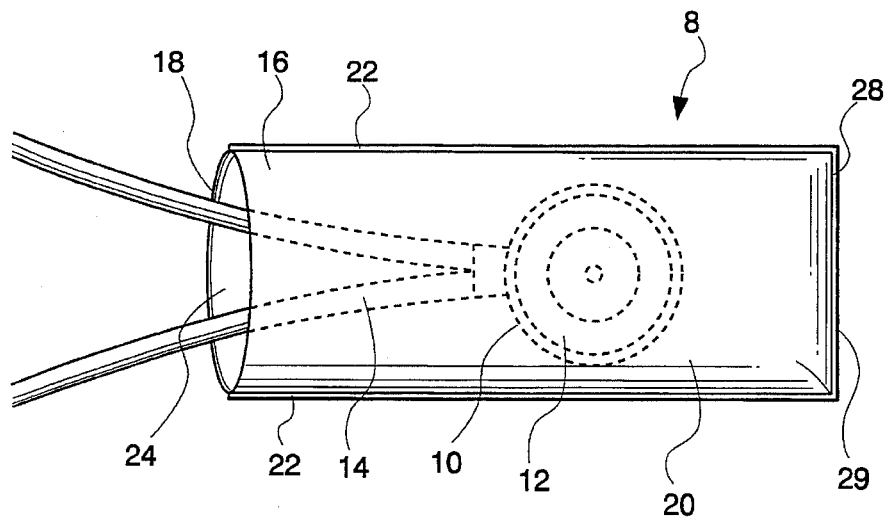
FIG. 1 is a perspective view of the kit of the present invention comprising a stethoscope bag and stethoscope.

Turning now to the drawings, FIG. 1 shows the combination of the invention which is a medical examination kit 8 comprising a stethoscope 10 and stethoscope protecting bag 20, wherein the bag is adapted to receive the head 12 and lower portions 14 of the stethoscope 10. Reference herein to the "head and lower portions" of a stethoscope means that portion of the stethoscope comprising the diaphragm and bell of the stethoscope and at least a portion of the tubes connecting the stethoscope head to the earpieces. The present invention also entails stethoscope protecting bags adapted to house or contain at least the head of a stethoscope during stethoscopic examination of a patient.

In its several embodiments, a stethoscope protecting bag of the present invention, when laying flat, may be formed of two generally rectangular panels, a front panel 16 and a rear panel 18, which are connected to one another along each of two lateral edges with lateral edge heatseals 22, and along a distal edge with a transverse heatseal 28 which provides a closed end 29. An open end 24 is suitable for receiving the head 12 of stethoscope 10. Thus a stethoscope protecting bag may be made conventionally from a length of flexible, plastic tubular extrusions, for example by welding sheets of plastic material (front and rear panels) along their lateral edges and closing the distal end with a transverse weld.

Stethoscope protecting bags of the present invention are preferably made of a thin, flexible, polymeric material such as polyethylene, latex rubber, silicone, soft vinyl, urethane, cellophane and the like as is well known in the art. The stethoscope-protecting bag of the present invention is generally rectangular in shape and the dimensions of the bag may be somewhat variable as long as the bag is appropriately sized for receiving the head of a stethoscope. Bags of approximately 2 to 8 centimeters in width and 5 to 30 centimeters in length would be of an appropriate size.

In one embodiment of the present invention, the stethoscope protecting bag 20 may be dimensioned so that the head 12 of a stethoscope 10 fits loosely inside the bag throughout its entire length. The stethoscope head may be grasped "through the bag" and the thin polymeric bag material manually gathered about the head of the stethoscope, if desired, so that the material lies flat against the diaphragm of the stethoscope when it is applied to an area on the patient's body.

The polymeric bag material preferably has a thickness of from about 0.1 to about 5 mils (i.e., between about 0.0001 and 0.005 inches), more preferably between about 0.5 mils and 2 mils. The bag material must, of course, be impermeable to bodily fluids. Surprisingly, a polymeric material of such thickness does not significantly impede or degrade the fidelity of sound transmission to the stethoscope. Various pliable plastics and other polymeric materials which are conventional in surgical and other medical applications are well known to the person of ordinary skill in the art and may be readily adapted for use in accordance with the present invention.

Figure 2A:
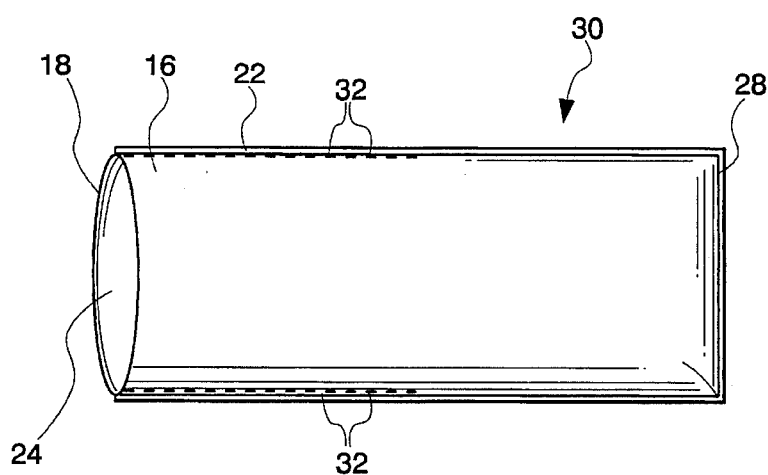
FIG. 2A is a perspective view of the stethoscope bag of the invention comprising perforated lateral edges.
Figure 2B:
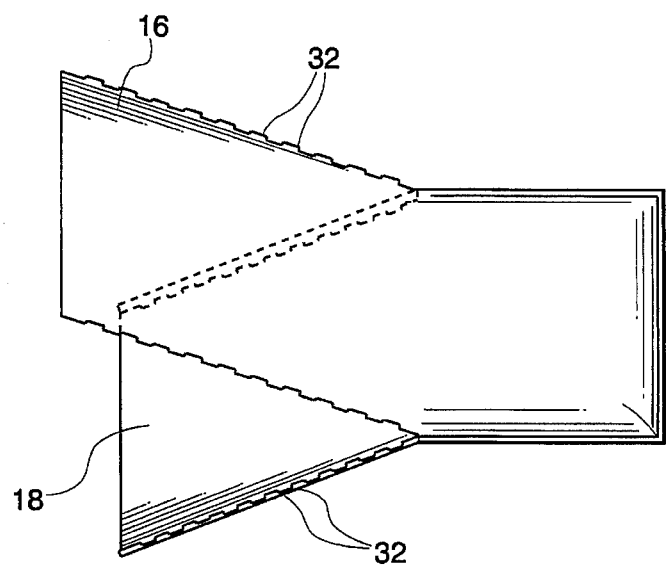
FIG. 2B is a perspective view of a stethoscope bag described in FIG. 2A showing the panels after separation along the perforated lateral edges.

In another of its embodiment the present invention entails a stethoscope protecting bag 30, as shown in FIGS. 2A and 2B, which is provided with lines of weakness 32 for separating the front panel 16 from the rear panel 18. The separation of front and rear panels 16, 18 facilitates removal of the bag after use without having to touch any portion of the bag which may have become contaminated during the examination. In presently preferred embodiments of the invention, longitudinal lines of weakness 32, such as perforations, are provided on, or adjacent and parallel to, the lateral edge heatseals 22. While the lateral lines of weakness 32 may extend from open end 24 to the closed end 29, preferably the lines of weakness do not extend to the lower portion of the bag which is intended to contact the patient's body. FIG. 2B depicts a stethoscope protecting bag having front panel 16 partially separated from the rear panel 18.

Figure 3A:
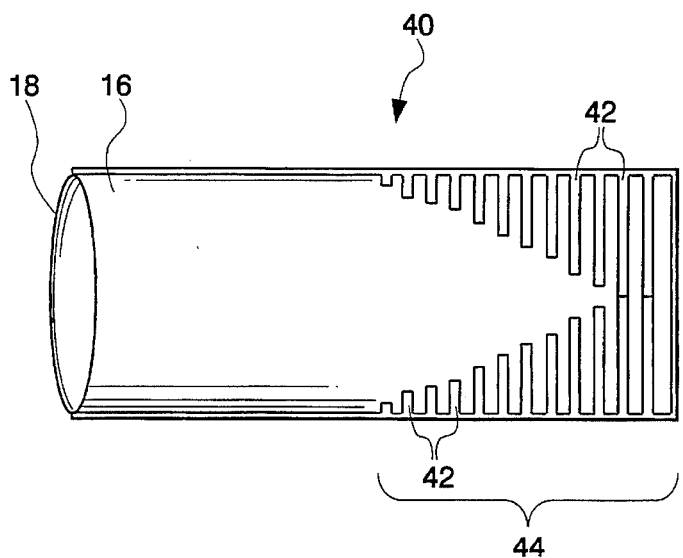
FIGS. 3A–3C show a perspective view of: (A) a stethoscope protecting bag having constriction seals of incrementally increasing length; (B) a stethoscope protecting bag having a pair of inwardly angling constriction seals; and (C) a stethoscope protecting bag having a plurality of disc-shaped constriction seals, as well as optional lateral lines of weakness.
Figure 3B:
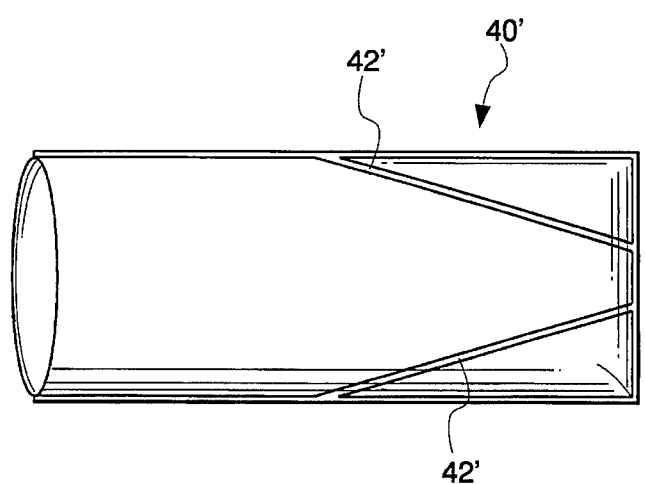
Figure 3C:
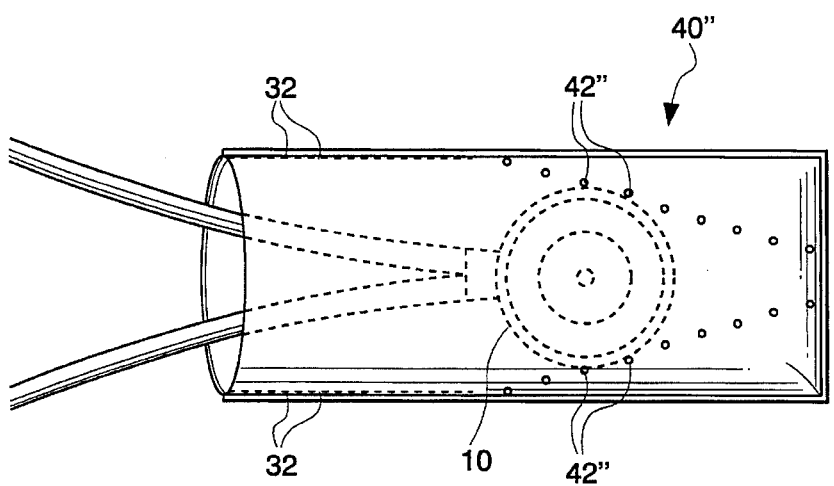

Turning to FIGS. 3A≠C, in another of its embodiments the present invention entails a stethoscope protecting bag 40 which has a portion of its interior dimensions decreased and which is elastically and resiliently deformable so that the stethoscope head can be wedged into the bag to prevent the bag from slipping off. With reference to FIGS. 3A–C, in this embodiment of the invention, the front and rear panels 16, 18 of bag 40 are further joined (e.g., heatsealed) with one or more constriction seal means 42 for decreasing the interior dimensions of the bag, the constriction seal means being suitably disposed relative to the lateral edge heatseals 22 so as to reduce or step-down the interior dimensions of the bag at a point which is sufficiently spaced apart from closed end of the bag, so that advancement of the stethoscope is impeded before it reaches the closed end. Then, further urging the stethoscope head into the stepped down portion 44 of bag 40 causes the bag to elastically deform and the stethoscope becomes engaged by the interior walls of the bag and retained due to the resilient nature of the bag material. In embodiments of the present invention which utilize a bag made of polymeric material which is resiliently deformable, it should be appreciated that the degree of resiliency may vary substantially so long as the bag is at least capable of being maintained on the stethoscope without becoming disengaged by its own weight. Elastically deformable and resilient polymeric materials such as polyethylene and other plastics, latex rubber, and the like are well known to those of ordinary skill in the art. A presently preferred material is polyethylene as is conventional in the plastic bag industry.

FIGS. 3A–C depict various embodiments of stethoscope protecting bags of the invention wherein the inside dimensions of the protective bag are decreased using one or more constriction seals 42. The constriction seals may be provided by one of more suitable placed welds or heatseals of a variety of suitable size and shape. FIG. 3A shows a plurality of opposing constriction seals 42 oriented perpendicular to the lateral edges of the bag 40 and having incrementally increasing lengths such that the inside diameter of the bag is incrementally stepped-down. This allows for the accommodation of variously sized stethoscopes. FIG. 3B depicts protective bag 40' having a pair of constricting seals 42' which converge toward each other in the direction of closed end of the bag. FIG. 3C shows a protective bag 40" having a plurality of disc-shaped heatseals 42". The constriction seals can be provided in a variety of other patterns, e.g., curved, parabolic, saw-toothed, etc. As will be appreciated by the person of ordinary skill, a wide variety of such patterns of constriction seals should be suitable for decreasing the inside dimension of a stethoscope protecting bag, and may be provided by sealing together the front and rear panels of a stethoscope protecting bag at one of more positions medial to at least one of the lateral edges of the bag.

Figure 4A:
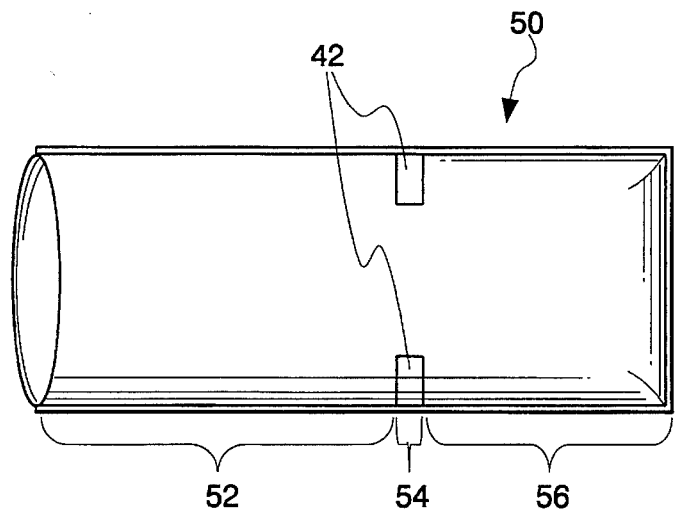
FIGS. 4A–4C show a perspective view of: (A) a stethoscope protecting bag having a first length of bag, a second length of bag and an area of reduced interior dimensions therebetween which area of reduced interior dimensions is capable of being resiliently deformed by passage of a stethoscope head therethrough; (B) a stethoscope protecting bag shown at a point where the stethoscope head elastically deforms the bag at the area of reduced interior dimensions; and (C) a stethoscope protecting bag with the stethoscope head contained within the second length of the bag.
Figure 4B:
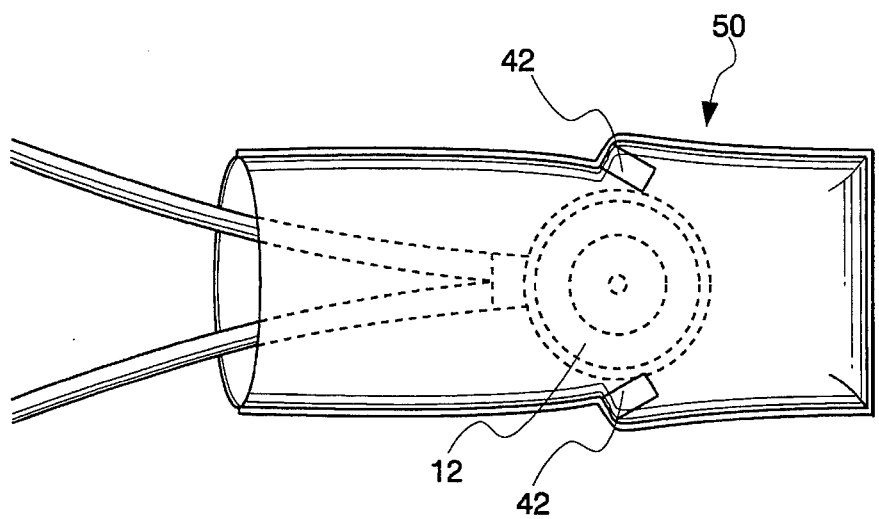
Figure 4C:
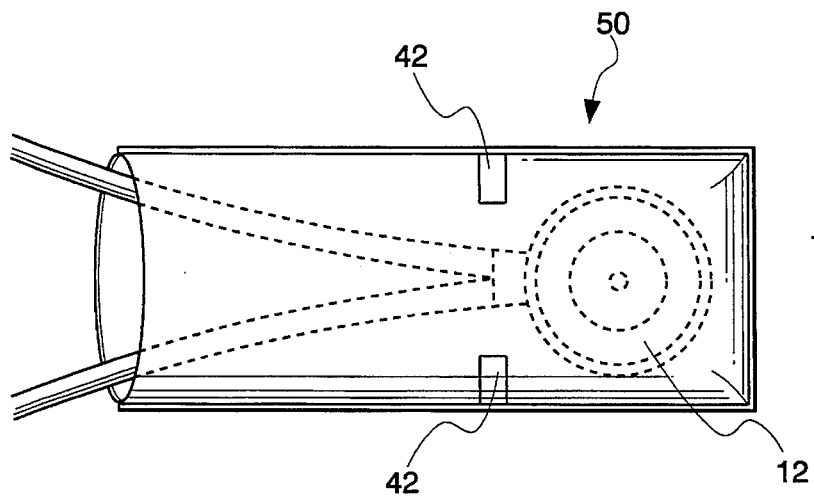

FIGS. 4A–C show another embodiment of the invention entailing a stethoscope protecting bag 50 having a first length of bag 52 for receiving the head of a stethoscope, an area of reduced interior dimensions 54, and a second length of bag 56 for housing the stethoscope head, wherein the stethoscope head must elastically deform the area of reduced interior dimensions 54, in order to enter the second length 56 having an inside diameter sized for receiving the stethoscope head. The area of reduced interior dimensions is provided by one or more constriction seals 42. By the phrase suitable for (or sized for) receiving the stethoscope head is meant that the interior dimensions are sufficiently great that no elastic deformation of the bag is needed to allow the stethoscope head to advance in the bag, in contrast to the area of reduced interior dimensions 54. The interior dimension in the first length and the second length of the bag may conveniently be approximately the same. In this embodiment of the invention, as the stethoscope head is urged past the constriction seal(s) 42, the stethoscope head "snaps" past the area of reduced dimensions 54 and into the second length 56 of the bag. Stethoscope protecting bag 50 may be pulled off with the stethoscope head 12 being retained within the second length of the bag until sufficient pulling force is exerted to "snap" the stethoscope head past "narrowed" area 54.

Figure 5A:
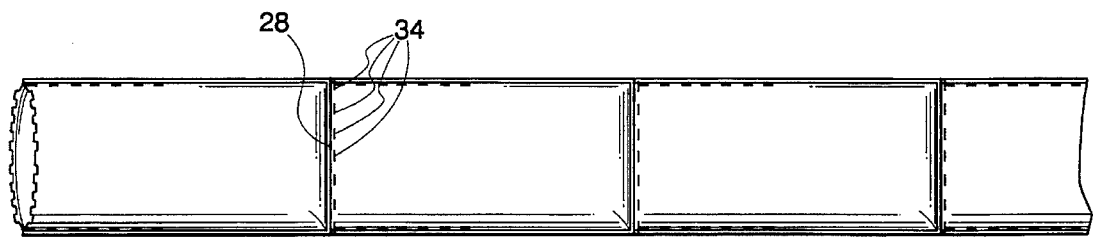
FIGS. 5A and 5B depict: (A) a continuous length of stethoscope protecting bags of the invention in head-to-tail arrangement with transverse perforations for separation of the individual bags; and (B) the continuous length of stethoscope protecting bags with a first bag separated along the transverse perforations from the remaining length of bags.
Figure 5B:
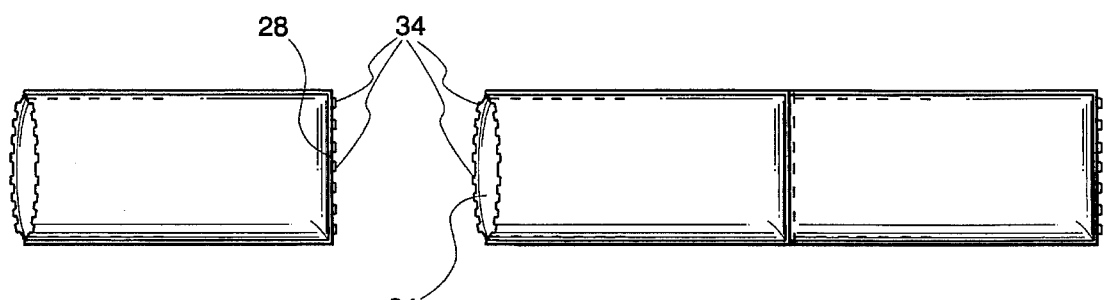

Referring now to FIGS. 5A and 5B, a plurality of individual bags oriented in head-to-tail fashion may be provided from a continuous length of polymeric tubular extrusion by a series of transverse heatseals 28 (i.e., welds) at predetermined intervals. Means for separating the bags may be provided by a series of transverse lines of weakness 34, such as perforations, which are disposed distal to, and parallel to, with the closed ends 29. See FIG. 5. A transverse line of weakness 34 also provides an open end 24 of a second bag, when the first and second contiguous bags are separated, as depicted in FIG. 5B. Other convenient packaging arrays may be utilized, such as cardboard books (analogous to match books) where the stethoscope protecting bags may be layered on top of each other and may be removed by tearing along a line of weakness 34. These packages can easily be kept in one's pocket or at the patient's bedside.

While stethoscope-protecting bags of the present invention do not have to be sterile, bags may be provided, using any suitable sterilization method known for disposable, plastic medical or surgical supplies (e.g., radiation, ethylene oxide, etc.). Because the stethoscope protecting bags of the present invention are simple to use and easy to manufacture with standard plastic (bag) or latex-rubber manufacturing technology, they will readily permit patients, physicians and nurses additional protection from disease transmission.

Use of a stethoscope protecting bag of the present invention is simple. The head 10 of the stethoscope is fed (e.g., by gravity) into a stethoscope protecting bag to a point where the stepped-down inside diameter, if present, impedes further progress. Then, by grasping the head of the stethoscope through a panel of the bag with one hand and alternatingly pulling on the lateral edges of the bag with the other hand, the stethoscope head may be urged further into the bag, causing the polymeric bag material to give slightly (elastically deform), thereby wedging the stethoscope inside the bag, or in an above described alternative embodiment, allowing the stethoscope head to enter and be retained within, the second length of bag. In those embodiments of the invention wherein the stethoscope head is retained in the bag by elastic force, the bag may be easily peeled away from the stethoscope head by simply pulling the open end of the bag and causing the bag to turn inside-out on itself. Desirably perforations 32 may be provided with any of the above described embodiments to facilitate removal.

The present invention allows a physician or nurse to use his or her own high quality stethoscope, without fear of soiling or contaminating it, and thus of spreading the contaminated material to themselves or to other patients. This will have great applications, particularly for use with very ill patients in intensive care units, patients with infectious diseases, patients who have open wounds or other sources of drainage of bodily fluids, or patients who are post-operative. While the invention has been described with some specificity, modifications apparent to those with ordinary skill in the art may be made without departing from the spirit of the invention.

Various features of the invention are set forth in the following claims.

What is claimed:

1. A stethoscope-protecting bag for protecting a stethoscope from becoming contaminated during a stethoscopic examination of an animal, the stethoscope-protecting bag comprising a length of flexible tubular polymeric material defining a first rectangular panel and a second rectangular panel which are joined at their lateral edges, the tubing being open at a first end and closed at a second end, the bag further comprising lines of weakness extending from the open end for at least a portion of the length of the bag, the lines of weakness being disposed substantially parallel to and adjacent to the joined lateral edges, whereby the first and second rectangular panel may be separated along the lines of weakness.

2. A stethoscope-protecting bag for protecting a stethoscope from becoming contaminated during a stethoscopic examination of an animal, the stethoscope-protecting bag comprising a length of flexible tubular polymeric material defining a first rectangular panel and a second rectangular panel which are joined at their lateral edges, the tubing being open at a first end and closed at a second end, the bag further comprising at least one constriction seal means for constricting the interior dimension of the bag, the constriction seal means decreasing the interior dimensions of the bag sufficiently such that the inner walls of the bag are capable of engaging a stethoscope head.

3. A stethoscope-protecting bag for protecting a stethoscope from becoming contaminated during a stethoscopic examination of an animal, the stethoscope-protecting bag comprising a length of flexible tubular polymeric material defining a first rectangular panel and a second rectangular panel which are joined at their lateral edges, the tubing being open at a first end and closed at a second end, the bag having a first length of tubing extending from the open end for receiving the head of a stethoscope, a second length of tubing extending to the closed end for housing the stethoscope head, and an area of reduced interior dimensions therebetween, wherein the stethoscope head must elastically deform the area of reduced interior dimensions to enter the second length of tubing.

4. A stethoscope protecting bag according to claim 2 further comprising lines of weakness extending from the open end for at least a portion of the length of the bag, the lines of weakness being disposed substantially parallel to and adjacent to the joined lateral edges.

5. A stethoscope protecting bag according to claim 3 further comprising lines of weakness extending from the open end for at least a portion of the length of the bag, the lines of weakness being disposed substantially parallel to and adjacent to the joined lateral edges.

6. A medical examination kit comprising:
   (i) a stethoscope having a head portion with a diaphragm capable of transducing bodily sounds; and
   (ii) a stethoscope-protecting bag comprising a length of flexible tubular polymeric material which when laying flat defines a first panel and a second panel which panels are generally rectangular and are attached to one another along each of two lateral edges, the length of flexible polymeric material having a substantially continuous interior wall defining an interior space sufficient to house at least the head of the stethoscope, the flexible tubular material having a first transverse end which is open to the interior space and a second transverse end which is closed to the interior space, the opening of the first transverse end being suitably sized to receive the head portion of the stethoscope, wherein the polymeric material is impermeable to bodily fluids and is capable of transmitting bodily sound without substantial adverse affect on sonic quality when a portion of the polymeric material is disposed between the diaphragm of the stethoscope and a portion of a human body.

7. An examination kit according to claim 6, wherein the bag is a stethoscope protecting bag further comprises lines of weakness extending from the open end for at least a portion of the length of the bag, the lines of weakness being disposed substantially parallel to and adjacent to the joined lateral edges.

8. An examination kit according to claim 6, wherein the first panel and second panel of the stethoscope protective bag are further attached at at least one point medial to the attached lateral edges so as to define an area of decreased interior dimensions, the stethoscope protecting bag being elastically deformable to engage the stethoscope head when it is urged into the area of decreased interior dimension.

9. An examination kit according to claim 6, wherein the stethoscope protecting bag comprises a first length of tubing extending from the open end for receiving the head of a stethoscope, a second length of tubing extending to the closed end for housing the stethoscope head, and an area of reduced interior dimensions therebetween, wherein the stethoscope head must elastically deform the area of reduced interior dimensions to enter the second length of tubing.

* * * * *